United States Patent
Wachtler et al.

(10) Patent No.: US 8,246,942 B2
(45) Date of Patent: Aug. 21, 2012

(54) MICROBICIDAL COMPOSITIONS

(75) Inventors: Peter Wachtler, Krefeld (DE); Martin Kugler, Leichlingen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 13/037,444

(22) Filed: Mar. 1, 2011

(65) Prior Publication Data

US 2012/0035228 A1 Feb. 9, 2012

Related U.S. Application Data

(63) Continuation of application No. 12/469,344, filed on May 20, 2009, now abandoned, which is a continuation of application No. 10/204,821, filed as application No. PCT/EP01/01497 on Feb. 12, 2001, now abandoned.

(30) Foreign Application Priority Data

Feb. 24, 2000 (DE) .................................. 100 08 507

(51) Int. Cl.
C23F 11/00 (2006.01)
A61L 11/00 (2006.01)
A61L 9/01 (2006.01)
C11D 3/48 (2006.01)
A01N 33/26 (2006.01)
A01N 31/08 (2006.01)
C02F 1/76 (2006.01)
C02F 1/68 (2006.01)
C09K 3/00 (2006.01)

(52) U.S. Cl. ................. 424/76.8; 422/1; 422/7; 422/14; 422/28; 422/40; 424/76.5; 510/108; 510/386; 210/749; 210/754; 210/764; 252/106; 252/393; 252/380; 252/1; 514/1; 514/731; 514/728; 514/150; 514/788

(58) Field of Classification Search .................. 422/1, 7, 422/14, 28, 32, 34, 363, 40; 424/76.5, 76.8; 510/108, 386; 210/749, 754, 764; 252/106, 252/393, 380, 1; 514/1, 731, 728, 150, 740, 514/788

See application file for complete search history.

(56) References Cited

U.S. PATENT DOCUMENTS

| | | | |
|---|---|---|---|
| 3,592,893 A | 7/1971 | Nosler et al. | |
| 3,829,305 A | 8/1974 | Brink, Jr. et al. | |
| 4,800,196 A | 1/1989 | Nomura et al. | |
| 4,939,266 A | 7/1990 | Bayer et al. | |
| 5,464,851 A * | 11/1995 | Morpeth | 514/373 |
| 5,641,808 A | 6/1997 | Gaffney et al. | |
| 5,681,852 A | 10/1997 | Bissett | |
| 2004/0236291 A1 | 11/2004 | Zelickson et al. | |

FOREIGN PATENT DOCUMENTS

| | | |
|---|---|---|
| DT | 2524543 | 6/1975 |
| EP | 0 095 907 A2 * | 12/1983 |
| EP | 0147222 A2 | 7/1985 |
| EP | 0513637 A2 | 11/1992 |
| GB | 2354771 A | 4/2001 |

OTHER PUBLICATIONS

European Search Report from co-pending Application EP04026053 dated Dec. 22, 2004, 5 pages.
Matotosum et al; Katayana Chemical Works Company, Japan; XP002184133; "Synergistic industrial microbicides containing isothiazolones and o-phenylphenol" Oct. 1, 1996.
Suzuki, et al.; Nippon Soda K.K., Japan; XP-002175723; "Toilet flushing waster containing bactericides and fungicides" Feb. 2, 1992.
Fuji Photo Film Co. Ltd,; XP-002184134; "Silver halide photographic photosensitive material—includes substitute phenyl polyoxyethylene and at least two of thiazolidine-one, nitro-bromo ethanol compound., and/or metal salt of substitute phenol" Jun. 4, 1991.
Morimoto et al.; Konica Company, Japan'; XP-002175724; "Antimicrobial and anticlogging ink-jet inks" Aug. 15, 2000.
Kull et al. CIBA Pharmaceutical Products, Inc. Summit, NJ; "Mixtures of Quaternary Ammonium Compounds and Long-chain Fatty Acids as Antifungal Agents" (1961) pp. 538-541.

* cited by examiner

*Primary Examiner* — Jill Warden
*Assistant Examiner* — Monzer Chorbaji
(74) *Attorney, Agent, or Firm* — Michael A. Miller

(57) ABSTRACT

The invention relates to synergistic mixtures of o-phenylphenol with other microbicidally active compounds, such as bronopol (2-bromo-2-nitro-1,3-propanedial), 2-methyl-2H-isothiazol-3-one, 1,2-dibromo-2,4-dicyanobutane.

10 Claims, No Drawings

MICROBICIDAL COMPOSITIONS

This application is a continuation of U.S. patent application Ser. No. 12/469,344 filed May 20, 2009, which is a continuation of U.S. patent application Ser. No. 10/204,821 filed Aug. 23, 2002, now abandoned, incorporated herein by reference.

The present invention provides microbicidal compositions having improved bactericidal activity. The invention relates to synergistic mixtures of o-phenylphenol (OPP) with other microbicidally active compounds, such as, for example, bronopol (2-bromo-2-nitro-1,3-propanediol), MIT (2-methyl-2H-isothiazol-3-one), Tektamer 38 (1,2-dibromo-2,4-dicyanobutane).

o-Phenylphenol (OPP) is a known active compound. It is used for industrial preservation and disinfection. The activity spectrum of OPP includes both gram-positive and gram-negative bacteria, and also fungi and yeasts. In spite of this overall good microbiological activity spectrum, the use concentration required in practice for controlling certain types of microorganisms (for example bacteria from the family of the Pseudomonadaceae) is not always entirely satisfactory from an economical and ecological point of view. There is therefore a need for broadly active microbicidal compositions which have a more even action against the microorganisms to be controlled and which can additionally be incorporated without any problems into a large number of substrates to be protected.

Surprisingly, it has now been found that active compound mixtures of OPP and at least one further bactericide, in particular in specific mixing ratios, have an unexpectedly high, synergistically enhanced activity. As a consequence, the amounts of active compound to be employed for protecting industrial products can be reduced, resulting in more economical use or in a contribution to increased preservation quality. In principle, it can be stated that the mixtures according to the invention are an improvement compared to the prior art, i.e. the use of the individual active compounds. The novel active compound mixtures are preferably used to preserve functional liquids and water-containing industrial products susceptible to attack by microorganisms.

The active compound mixtures according to the invention can be used, for example, for protecting the following industrial products:

starch solutions, dispersions or slurries or other starch-based products, such as, for example, thickeners used in printing slurries of other raw materials such as color pigments (for example, iron oxide pigments, carbon black pigments, titanium dioxide pigments) or slurries of fillers such as kaolin or calcium carbonate concrete additives, for example those based on molasses or ligninosulfonates glues and adhesives based on the known raw materials of animal, vegetable or synthetic origin bitumen emulsions detergents and cleaners for industrial and domestic use mineral oils or mineral oil products (such as, for example diesel fuels)

auxiliaries for the leather, textile or photochemical industry precursors and intermediates of the chemical industry, for example in the production and storage of dyestuffs solvent borne or water borne inks wax and clay emulsions Bacterial mixing partners for OPP that may be mentioned are the compounds bronopol (2-bromo-2-nitro-1,3-propanediol)
MIT (2-methyl-2H-isothiazol-3-one)
Tektamer 38 (1,2-dibromo-2,4-dicyanobutane).

The mixing ratio of o-phenylphenol (OPP) to the other bactericidally active component can be varied within a wide range, the optimum depending, for example, on the bactericidal mixing partner used, but also on the application in question.

In preservatives having broad antimicrobial action used for protecting functional liquids and water-containing industrial products, the weight ratio of o-phenylphenol (OPP) to the mixing partner should be from 99.9:0.1 to 50:50, preferably from 99:1 to 70:30, particularly preferably from 80:20 to 60:40.

The active compound combinations according to the invention are highly active against microorganisms. The active compound combinations according to the invention are used in the protection of materials for protecting industrial materials, in particular for protecting aqueous functional liquids; they act against bacteria and molds, and also against yeast and slime organisms. The following microorganisms may be mentioned by way of example, without imposing any limitations:

*Alternaria*, such as *Alternaria tenuis*, *Aspergillus*, such as *Aspergillus niger*, *Chaetomium*, such as *Chaetomium globosum*, *Fusarium*, such as *Fusarium solani*, *Lentinus*, such as *Lentinus tigrinus*, *Penicillium*, such as *Penicillium glaucum*; *Alcaligenes*, such as *Alcaligenes faecalis*, *Bacillus*, such as *Bacillus subtilis*, *Escherichia*, such as *Escherichia coli*, *Pseudomonas*, such as *Pseudomonas aueruginosa* or *Pseudomonas fluorescens*, *Staphylococcus*, such as *Staphylococcus aureus*; *Candida*, such as *Candida albicans*, *Geotrichum*, such as *Geotrichum candidum*;

Depending on their respective physical and/or chemical properties, the active compound combinations according to the invention can be added either separately, in the form of the individual active compounds, where it is possible, depending on the present preservation problem, to adjust the concentration ratio individually, or they can be converted into customary formulations, such as solutions, emulsions, suspensions, powders, foams, pastes, granules, aerosols or microencapsulations in polymeric substances.

These formulations are prepared in a manner known per se, for example by mixing the active compounds with extenders, i.e. liquid solvents, liquefied gases under pressure and/or solid carriers, if appropriate with the use of surfactants, i.e. emulsifiers and/or dispersants and/or foam formers. If the extender used is water, it is also possible to use, for example, organic solvents as auxiliary solvents. Essentially, suitable liquid solvents include: aromatic compounds, such as xylene, toluene, alkylnaphthalenes, chlorinated aromatic compounds or chlorinated aliphatic hydrocarbons, such as chlorobenzenes, chloroethylenes, or methylene chloride, aliphatic hydrocarbons, such as cyclohexane or paraffins, for example mineral oil fractions, alcohols, such as butanol or glycol or ethers and esters thereof, ketones, such as acetone, methyl ethyl ketone, methyl isobutyl ketone or cyclohexanone, strongly polar solvents, such as dimethylformamide or dimethyl sulfoxide, and also water; liquefied gaseous extenders or carriers are to be understood as meaning liquids which are gaseous at ambient temperature and under atmospheric pressure, for example aerosol propellants, such as halogenated hydrocarbons and also butane, propane, nitrogen and carbon dioxide; suitable solid carriers are: for example ground natural minerals, such as kaolins, clays, talc, chalk, quartz, attapulgite, montmorillonite or diatomaceous earth, and ground synthetic minerals, such as finely divided silica, aluminum oxide and silicates; suitable solid carriers for granules are: for example crushed and fractionated natural rocks, such as calcite, marble, pumice, sepiolite and dolomite, and also synthetic granules of inorganic and organic meals, and granules of organic material such as sawdust, coconut shells, corn cobs and tobacco stalks; suitable emulsifiers and/or foam formers are: for example nonionic and anionic emulsifiers, such as polyoxyethylene fatty acid esters, polyoxyethylene fatty alcohol esters, for example alkylaryl polyglycol ethers, alkylsulfonates, alkyl sulfates, arylsulfonates, and also protein hydrolyzates; suitable dispersants are: for example lignosulfide waste liquors and methyl cellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins and synthetic phospholipids can be used in the formulations. Other possible additives are mineral and vegetable oils.

The microbicidal compositions or concentrates used for protecting the industrial materials comprise the active compound combination in a concentration of from 0.1 to 95% by weight, and in particular from 5 to 50% by weight.

The use concentrations of the active compound combinations to be used according to the invention depend on the nature and the occurrence of the microorganisms to be controlled and on the composition of the material to be protected. The optimum amount for use can be determined by test series. In general, the use concentrations are in the range from 0.01 to 5% by weight, preferably from 0.05 to 2.0% by weight, based on the material to be protected.

The active compound combinations according to the invention show synergistic effects, i.e. the activity of the mixture is greater than the activity of the individual components.

The observed synergism of the active compound mixtures, claimed in the present application, consisting of o-phenylphenol (OPP) and other bactericides can be determined by the following mathematical equation (see F. C. Kull, P. C. Elisman, H. D. Sylwestrowicz and P. K. Mayer, Appl. Microbiol. 9, 538 (1960):

$$\text{synergistic index } (SI) = \frac{Q_a}{Q_A} + \frac{Q_b}{Q_B}$$

where $Q_a$=the amount of component A in the active compound mixture which achieves the desired effect, i.e. no microbial growth.

$Q_A$=the amount of component A which, when used on its own, suppresses the growth of the microorganisms.

$Q_b$=the amount of component B in the active compound mixture which suppresses the growth of the microorganisms.

$Q_b$=the amount of component B which, when used on its own, suppresses the growth of the microorganisms.

A synergistic index of <1 indicates a synergistic effect for the active compound mixture.

The synergistically enhanced activity is documented by way of example, without imposing any limitation, by the examples below.

EXAMPLE 1

Mixture OPP/BNPD

Bronopol

Determination of the Minimum Inhibitory Concentration (MIC) of Compositions According to the Invention Against *Pseudomonas fluerescens*

| Active compound or active compound mixture (weight ratios) | MIC value against *Pseudomonas fluorescens* [in mg/l] | SI |
|---|---|---|
| OPP 100% active compound | 500 | |
| BNPD 100% active compound | 35 | |
| OPP/BNPD (9:1) | 200 | 0.93 |
| OPP/BNPD (4:1) | 100 | 0.73 |
| OPP/BNPD (2.3:1) | 50 | 0.49 |
| OPP/BNPD (1.5:1) | 50 | 0.63 |

The mixtures according to the invention have pronounced synergistic activity.

EXAMPLE 2

Mixture OPP/Tektamer 38

1,2-dibromo-2,4-dicyanobutane

Determination of the Minimum Inhibitory Concentration (MIC) of Compositions According to the Invention Against *Pseudomonas fluerescens*

| Active compound or active compound mixture (weight ratios) | MIC value against *Pseudomonas fluorescens* [in mg/l] | SI |
|---|---|---|
| OPP (100% active compound) | 500 | |
| Tektamer 38 (100% active compound) | 100 | |
| OPP/T. 38 (9:1) | 200 | 0.56 |
| OPP/T. 38 (4:1) | 100 | 0.36 |
| OPP/T. 38 (2.3:1) | 100 | 0.44 |
| OPP/T. 38 (1.5:1) | 50 | 0.26 |

The combinations according to the invention have pronounced synergistic activity.

EXAMPLE 3

Mixture OPP/MIT 2-methyl-2H-isothiazolin-3-one

Determination of the Minimum Inhibitory Concentration (MIC) of Compositions According to the Invention Against *Pseudomonas fluerescens*

| Active compound or active compound mixture (weight ratios) | MIC value against *Pseudomonas fluorescens* [in mg/l] | SI |
|---|---|---|
| OPP (100% active compound) | 500 | |
| MIT (100% active compound) | 30 | |

-continued

| Active compound or active compound mixture (weight ratios) | MIC value against *Pseudomonas fluorescens* [in mg/l] | SI |
|---|---|---|
| OPP/MIT (9:1) | 100 | 0.51 |
| OPP/MIT (4:1) | 50 | 0.41 |
| OPP/MIT (2.3:1) | 35 | 0.38 |
| OPP/MIT (1.5:1) | 20 | 0.29 |

The combinations according to the invention have pronounced synergistic activity.

What is claimed is:

1. A microbicidal composition consisting essentially of a synergistic mixture of microbicidally active compounds, said synergistic mixture of microbicidally active compounds consisting of o-phenylphenol, 2-methyl-2H-isothiazol-3-one, and 1,2-dibromo-2,4-dicyanobutane.

2. A process for protecting industrial materials against attack by fungi and algae comprising applying thereto the composition according to claim 1.

3. A method for protecting industrial materials against attack by fungi and algae, comprising mixing or treating the industrial materials with a composition according to claim 1.

4. A process for preparing the composition according to claim 1, comprising mixing together the o-phehylphenol, the 2-methyl-2H-isothiazol-3-one, and the 1,2-dibromo-2,4-dicyanobutane.

5. The composition according to claim 1, wherein the ratio of o-phenylphenol to 2-methyl-2H-isothiazol-3-one and 1,2-dibromo-2,4-dicyanobutan is between 99.9:0.1 and 50:50 by weight.

6. The microbicidal composition according to claim 1, further comprising at least one extender, surfactant, tackifier, and/or mineral and/or vegetable oil.

7. A process for protecting industrial materials against attack by fungi and algae comprising applying thereto the composition according to claim 6.

8. A method for protecting industrial materials against attack by fungi and algae, comprising mixing or treating the industrial materials with a composition according to claim 6.

9. A process for preparing the composition according to claim 6, comprising mixing together the o-phehylphenol, the 2-methyl-2H-isothiazol-3-one, the 1,2-dibromo-2,4-dicyanobutane of the synergistic mixture of microbicidally active compounds and the at least one extender, surfactant, tackifier, and/or mineral and/or vegetable oil.

10. The composition according to claim 6, wherein the ratio of o-phenylphenol to 2-methyl-2H-isothiazol-3-one, 1,2-dibromo-2,4-dicyanobutane of the synergistic mixture of microbicidally active compounds, and the at least one extender, surfactant, tackifier, and/or mineral and/or vegetable oil is between 99.9:0.1 and 50:50 by weight.

* * * * *